United States Patent [19]
Viera

[11] Patent Number: 6,039,699
[45] Date of Patent: *Mar. 21, 2000

[54] STIFF CATHETER GUIDEWIRE WITH FLEXIBLE DISTAL PORTION

[75] Inventor: Fernando M. Viera, Hialeah, Fla.

[73] Assignee: Cordis Corporation, Miami Lakes, Fla.

[*] Notice: This patent issued on a continued prosecution application filed under 37 CFR 1.53(d), and is subject to the twenty year patent term provisions of 35 U.S.C. 154(a)(2).

[21] Appl. No.: 08/589,627

[22] Filed: Jan. 22, 1996

[51] Int. Cl.⁷ ..................................................... A61B 5/00
[52] U.S. Cl. ............................................. 600/585; 604/264
[58] Field of Search .................... 604/280–282, 604/96, 264, 265, 523, 524, 530, 525; 128/772, 657; 600/585

[56] References Cited

U.S. PATENT DOCUMENTS

| | | | |
|---|---|---|---|
| 4,721,117 | 1/1988 | Mar et al. | 128/772 |
| 4,757,827 | 7/1988 | Buchbinder et al. | 128/772 |
| 4,846,186 | 7/1989 | Box et al. | 128/657 |
| 4,940,062 | 7/1990 | Hampton et al. | 128/772 |
| 4,953,553 | 9/1990 | Tremulis | 128/637 |
| 5,009,655 | 4/1991 | Daignault, Jr. et al. | 606/7 |
| 5,141,494 | 8/1992 | Danforth et al. | 604/96 |
| 5,243,996 | 9/1993 | Hall | 128/772 |
| 5,267,573 | 12/1993 | Evans et al. | 128/772 |
| 5,345,945 | 9/1994 | Hodgson et al. | 128/772 |
| 5,372,144 | 12/1994 | Mortier et al. | 128/772 |
| 5,404,887 | 4/1995 | Prather | 128/772 |
| 5,409,015 | 4/1995 | Palermo | 128/772 |
| 5,480,382 | 1/1996 | Hammerslag et al. | 604/95 |
| 5,488,959 | 2/1996 | Ales | 128/772 |
| 5,498,250 | 3/1996 | Prather | 604/280 |
| 5,605,162 | 2/1997 | Mirzaee et al. | 128/772 |
| 5,666,969 | 9/1997 | Urick et al. | 128/772 |
| 5,706,826 | 1/1998 | Schwager | 128/772 |

FOREIGN PATENT DOCUMENTS

| | | |
|---|---|---|
| 0 382 974 A1 | 8/1990 | European Pat. Off. . |
| 0 611 073 A1 | 8/1994 | European Pat. Off. . |
| 0 652 026 A1 | 5/1995 | European Pat. Off. . |

*Primary Examiner*—Corrine McDermott
*Assistant Examiner*—Cris L. Rodriguez
*Attorney, Agent, or Firm*—Watts, Hoffmann, Fisher & Heinke

[57] ABSTRACT

A catheter guidewire has a relatively flexible distal portion to facilitate the steering of the guidewire through the cardiovascular system of a subject and the capability of the guidewire to reach a deposit region within a relatively tortuous portion of the cardiovascular system. The guidewire also has a relatively stiff proximal portion to facilitate the pushing of the guidewire through the cardiovascular system from an entry point of the subject. For one embodiment, the guidewire includes a corewire and a sleeve secured to the corewire such that the sleeve surrounds a proximal portion of the corewire. The sleeve is formed from a material having a relatively greater stiffness than the material for the corewire. The sleeve may be formed from stainless steel, for example, to provide for a relatively stiff proximal portion of a corewire formed from a material exhibiting superelastic properties, such as a nickel-titanium or Nitinol alloy for example.

22 Claims, 2 Drawing Sheets

STIFF CATHETER GUIDEWIRE WITH FLEXIBLE DISTAL PORTION

FIELD OF THE INVENTION

The present invention relates generally to the field of catheters. More particularly, the present invention relates to the field of catheter guidewires.

BACKGROUND OF THE INVENTION

Percutaneous angioplasty is a therapeutic medical procedure for increasing blood flow through a blood vessel.

For one known procedure, a guide catheter is inserted into the cardiovascular system of a patient and guided toward a region having accumulated deposits along the inner walls of a blood vessel. An elongated flexible guidewire is inserted into the guide catheter and guided beyond the distal end of the guide catheter through the cardiovascular system to the deposit region. As the path to the deposit region may be tortuous, the guidewire is typically flexible and bent to a desired configuration at a distal tip of the guidewire to facilitate steering of the guidewire into branching blood vessels. The guidewire typically has radiopaque regions viewable with an x-ray imaging system to monitor guidewire progress through the patient.

An elongated catheter having a deflated balloon is routed over the guidewire so as to position the deflated balloon in the deposit region. Once positioned, the balloon may be inflated to widen the passageway through the deposits in the blood vessel and therefore increase blood flow.

SUMMARY OF THE INVENTION

One object of the present invention is to provide for a guidewire that may be pushed through a subject with relative ease.

Another object of the present invention is to provide for a guidewire having a relatively stiff proximal portion and a relatively flexible distal portion.

Another object of the present invention is to provide for a guidewire having a relatively flexible corewire with a relatively stiff sleeve at a proximal portion of the corewire.

Another object of the present invention is to provide for a guidewire having a superelastic corewire with a relatively stiff sleeve at a proximal portion of the corewire.

In accordance with the present invention, a guidewire has an elongated corewire formed from a first material and an elongated sleeve secured to the corewire such that the sleeve surrounds at least a portion of the corewire. The sleeve is formed from a second material having a relatively greater stiffness than the first material. The first material may exhibit superelastic properties and may include an alloy having nickel and titanium. The second material may include stainless steel. The sleeve may be generally cylindrical in shape. The corewire may include a proximal segment and at least one segment that tapers toward a distal end of the corewire. The sleeve may surround at least a portion of the proximal segment, and a spring may be secured to the corewire such that the spring surrounds a distal segment of the corewire. The guidewire may be used in combination with a catheter.

Also in accordance with the present invention, a method for fabricating a guidewire includes steps of providing an elongated corewire formed from a first material, providing an elongated sleeve formed from a second material having a relatively greater stiffness than the first material, surrounding at least a portion of the corewire with the sleeve, and securing the sleeve to the corewire to fabricate the guidewire. The first material may exhibit superelastic properties and may include an alloy having nickel and titanium. The second material may include stainless steel. The sleeve may be generally cylindrical in shape. The corewire may be provided with a proximal segment and at least one segment that tapers toward a distal end of the corewire. The sleeve may surround at least a portion of the proximal segment, and a spring may be secured to the corewire such that the spring surrounds a distal segment of the corewire.

Other objects, features, and advantages of the present invention will be apparent from the accompanying drawings and from the detailed description that follows below.

BRIEF DESCRIPTION OF THE DRAWINGS

The present invention is illustrated by way of example and not limitation in the figures of the accompanying drawings, in which like references indicate similar elements and in which.

DETAILED DESCRIPTION

Figures 1, 2:
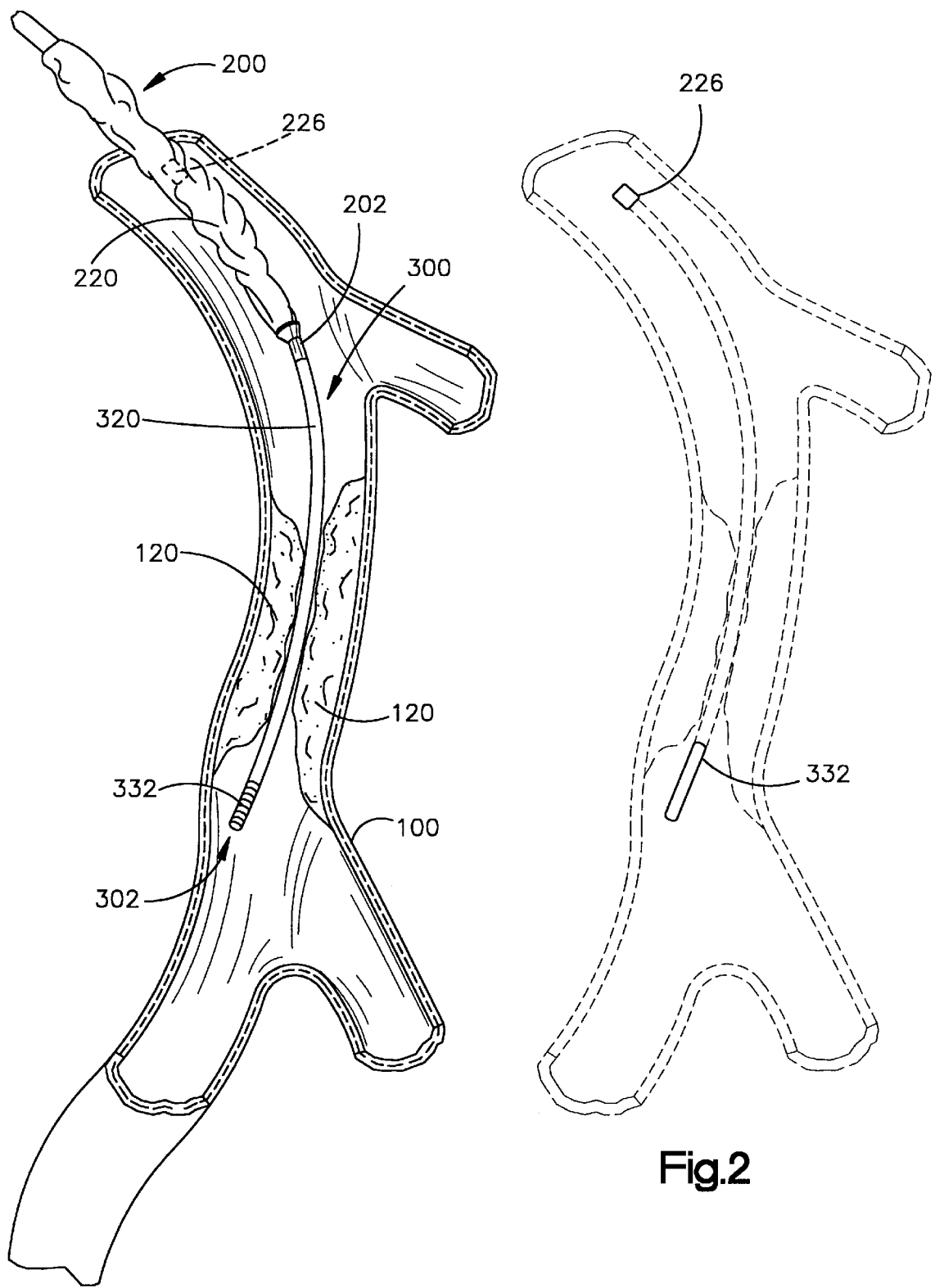
FIG. 1 illustrates a balloon catheter guided over a guidewire to a deposit region of a blood vessel.
FIG. 2 illustrates the catheter of FIG. 1 when viewed with an imaging system.

FIG. 1 illustrates a distal portion of an elongated catheter 200 being guided over an elongated guidewire 300 to a deposit region of a blood vessel 100 in the cardiovascular system of a subject. The deposit region of blood vessel 100 includes deposits 120 that have accumulated along the inner walls of blood vessel 100, restricting blood flow through blood vessel 100.

To guide catheter 200 to the deposit region, an elongated guide catheter is first inserted into an entry point of the subject and through the cardiovascular system of the subject toward the deposit region. A distal end 302 of guidewire 300 is inserted into the guide catheter at the entry point of the subject and routed beyond the distal end of the guide catheter through the cardiovascular system to the deposit region of blood vessel 100.

Figure 3:
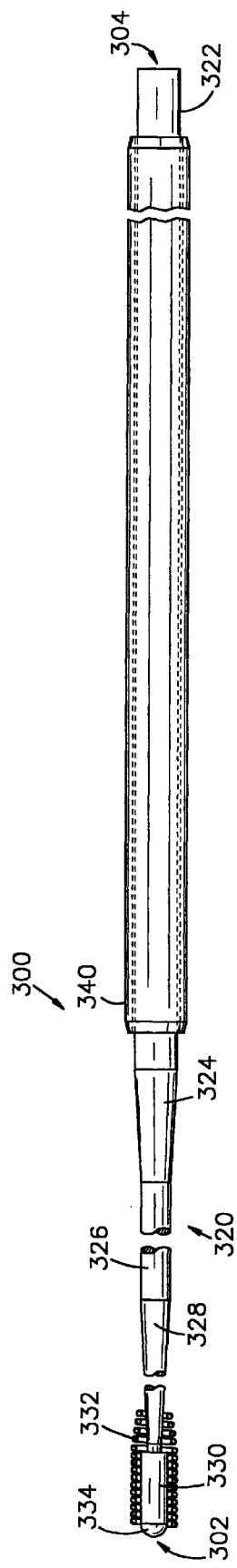
FIG. 3 illustrates the guidewire of FIG. 1.

Guidewire 300 includes an elongated corewire 320 and an elongated sleeve 340 surrounding at least a portion of corewire 320, as illustrated in FIG. 3. Corewire 320 and sleeve 340 may be formed from any suitable material to any suitable shape, width, and length depending, for example, on the size of the blood vessels through which guidewire 300 is to be guided and on the location of the deposit region from the entry point of the subject.

For one embodiment, as illustrated in FIG. 3, corewire 320 includes a proximal segment 322 having a substantially uniform diameter. Proximal segment 322 may have any suitable diameter and any suitable length, such as one that spans over three-fourths the overall length of corewire 320 for example. The remainder of corewire 320 tapers toward a distal segment 330 at distal end 302 of guidewire 300. Corewire 320 tapers from segment 322 along a segment 324 toward distal end 302 to a segment 326 having a substantially uniform diameter. Corewire 320 further tapers from segment 326 along a segment 328 to distal segment 330. Segments 324, 326, and 328 may be formed to any suitable length and diameter using a suitable centerless grinding technique, for example.

Corewire 320 may have a total length in the range of approximately 70 inches to approximately 120 inches, for example. Segment 322 may have a length in the range of approximately 53 inches to approximately 113 inches, for example, and may have a substantially uniform diameter in the range of approximately 0.007 inch to approximately 0.015 inch, for example. Segment 324 may have a length in the range of approximately 1 inch to approximately 3 inches, for example. Segment 326 may have a length in the range of approximately 5 inches to approximately 10 inches, for example. Segment 328 may have a length in the range of approximately 1 inch to approximately 3 inches, for example. Segments 324, 326, and 328 may taper toward distal end 302 to any suitable diameter.

Distal segment 330 is relatively flat and may be formed to any suitable dimensions using any suitable technique, such as by rolling or stamping the distal tip of the ground corewire 320. Distal segment 330 may have a width of approximately 0.005 inch, for example, may have a length in the range of approximately 0.3 inch to approximately 1.0 inch, for example, and may have a thickness in the range of approximately 0.001 inch to approximately 0.003 inch, for example.

A coiled wire spring 332 surrounds at least a portion of distal segment 330, as illustrated in FIG. 3. Spring 332 may also extend to surround at least a portion of segments 328, 326, 324, and/or 322 of corewire 320. The wire for spring 332 may have any suitable diameter and may be wound with any suitable pitch between windings. Spring 332 may be formed from any suitable material and may be secured to corewire 320 using any suitable technique. Spring 332 may be formed from a radiopaque material, such as platinum for example, and may be welded, brazed, or soldered to corewire 320. In welding, brazing, or soldering spring 332 to distal segment 330, a relatively smooth, hemispherical bead 334 may be formed at the tip of distal end 302, as illustrated in FIG. 3.

Corewire 320 may be formed from a relatively flexible material having a suitable lubricant coating or outer surface to facilitate the pushing and steering of corewire 320 through the cardiovascular system from the entry point of the subject. The tapering of this flexible material toward distal end 302 also facilitates the steering of corewire 320 through the subject and, in particular, through a relatively tortuous path leading to the deposit region of blood vessel 100.

The flexible material of corewire 320 further enables the bending and shaping of distal segment 330 to a desired configuration. As torque is applied to a proximal end 304 of guidewire 300 and transmitted to distal segment 330, the bent distal segment 330 may be oriented as desired to steer guidewire 330 in a suitable direction, such as into branching blood vessels for example, as may be necessary to reach the deposit region of blood vessel 100. Bead 334 helps to avoid damage to the inner walls of blood vessels as a result of contact with the tip of distal end 302. As illustrated in FIG. 2, an x-ray imaging system may be used to view radiopaque spring 332 and therefore monitor the orientation of the bent distal segment 330 as well as the progress of guidewire 300 as guidewire 300 is pushed and steered through the subject.

For one embodiment, corewire 320 may be formed from a suitable material exhibiting superelastic or superelastic-like properties to provide enhanced flexibility and the ability to bend distal segment 330 multiple times with minimized kinking. Corewire 320 may be formed from a suitable nickel-titanium ($Ni_xTi_y$) or Nitinol alloy, for example, and may be constructed in accordance with U.S. Pat. No. 5,402,799 to Colon et al., entitled GUIDEWIRE HAVING FLEXIBLE FLOPPY TIP. U.S. Pat. No. 5,402,799 is herein incorporated by reference. For other embodiments, corewire 320 may be formed from a plastic.

Sleeve 340 is configured to mate with corewire 320 in a coaxial manner so as to surround at least a portion of corewire 320, as illustrated in FIG. 3. Sleeve 340 may be formed to any suitable size and shape depending, for example, on the size and shape of corewire 320.

For one embodiment, as illustrated in FIG. 3, sleeve 340 is a hypodermic tube or hypotube that is generally cylindrical in shape and sized so as to snugly fit over the outer surface of proximal segment 322 and surround at least a portion of proximal segment 322. Sleeve 340 may have a length in the range of approximately 45 inches to approximately 105 inches, for example, an inner diameter in the range of approximately 0.008 inch to approximately 0.016 inch, for example, and a wall thickness in the range of approximately 0.001 inch to approximately 0.005 inch, for example.

Sleeve 340 may be formed from a material that is stiffer than the flexible material for corewire 320. One indication for stiffness, or resistance to elastic strain, may be the modulus of elasticity for the materials used for corewire 320 and sleeve 340. Sleeve 340 may be secured to corewire 320 using any suitable technique depending, for example, on the materials for corewire 320 and sleeve 340. Sleeve 340 may be secured to corewire 320 with an adhesive, for example, or may be welded, brazed, or soldered, for example, to corewire 320.

With sleeve 340 secured to surround a proximal portion of corewire 320, guidewire 300 has a relatively stiff proximal portion to facilitate the pushing of guidewire 300 through the subject and also has a relatively flexible portion toward distal end 302 to facilitate not only the steering of guidewire 300 through the subject but also the capability of guidewire 300 to reach the deposit region within a relatively tortuous portion of the cardiovascular system of the subject. Sleeve 340 may have a suitable lubricant coating or outer surface to facilitate the pushing of guidewire 300 through the subject. Sleeve 340 may be treated with a Teflon spray, for example, to lubricate the outer surface of sleeve 340.

For one embodiment with corewire 320 having superelastic or superelastic-like properties, sleeve 340 may be formed from stainless steel, for example, to compensate for any lack of stiffness of corewire 320 in pushing corewire 320 through the subject. Sleeve 340 may be formed from type 340 stainless steel, for example.

Although illustrated in FIG. 3 for use with corewire 320, sleeve 340 may also be used to provide for relatively stiff proximal portions of other corewires or guidewires, such as those disclosed in U.S. Pat. No. 5,402,799 and in U.S. Pat. No. 5,267,574 to Viera et al., entitled GUIDEWIRE WITH SPRING AND A HEAT SHRINKABLE CONNECTION. U.S. Pat. No. 5,267,574 is herein incorporated by reference.

To guide catheter 200 to the deposit region as illustrated in FIG. 1, catheter 200 includes a center passageway having a diameter of suitable size to accommodate guidewire 300. Guidewire 300 may be inserted into this center passageway at a distal end 202 of catheter 200, and catheter 200 may be guided over guidewire 300 through the guide catheter and beyond the distal end of the guide catheter to the deposit region.

Near distal end 202, catheter 200 has a deflated balloon 220 and a radiopaque marker band 226 positioned beneath balloon 220 as illustrated in FIG. 1. Catheter 200 includes another passageway extending from a proximal end of catheter 200 and along the length of catheter 200 to balloon 220 for carrying fluid, for example, to inflate balloon 220. Once balloon 220 is positioned between deposits 120 of blood vessel 100, balloon 220 may be inflated to widen the passageway through deposits 120 and therefore increase blood flow through blood vessel 100.

Guidewire 300 and catheter 200 may be positioned in the deposit region of blood vessel 100 by monitoring with an x-ray imaging system the progress of spring 332 and marker band 226, respectively, as illustrated in FIG. 2. For one technique, guidewire 300 is first pushed through the guide catheter and guided beyond the distal end of the guide catheter to the deposit region. Catheter 200 is then pushed over guidewire 300 through the guide catheter and beyond the distal end of the guide catheter to the deposit region. For another technique, guidewire 300 and catheter 200 are mated prior to insertion into the guide catheter and together guided beyond the distal end of the guide catheter to the deposit region by alternately advancing the guidewire 300 for a desired distance and pushing catheter 200 over the advanced portion of guidewire 300.

In the foregoing description, the invention has been described with reference to specific exemplary embodiments thereof. It will, however, be evident that various modifications and changes may be made thereto without departing from the broader spirit or scope of the present invention as defined in the appended claims. The specification and drawings are, accordingly, to be regarded in an illustrative rather than a restrictive sense.

What is claimed is:

1. A guidewire comprising:
    a) an elongated corewire formed from a first material; and
    b) an elongated sleeve secured to the corewire such that at least a majority length of the sleeve surrounds at least a portion of the corewire, the sleeve formed from a second material having a relatively greater stiffness than the first material.
2. The guidewire of claim 1, wherein the first material exhibits superelastic properties.
3. The guidewire of claim 2, wherein the first material includes an alloy having nickel and titanium.
4. The guidewire of claim 1, wherein the second material includes stainless steel.
5. The guidewire of claim 2, wherein the second material includes stainless steel.
6. The guidewire of claim 1, wherein the sleeve is generally cylindrical in shape.
7. The guidewire of claim 1, wherein the corewire includes a proximal segment and at least one segment that tapers toward a distal end of the corewire, and
    wherein at least the majority length of the sleeve surrounds at least a portion of the proximal segment.
8. The guidewire of claim 1, including a spring secured to the corewire such that the spring surrounds a distal segment of the corewire.
9. The guidewire of claim 1, in combination with a catheter.
10. A guidewire comprising:
    a) an elongated corewire formed from a first material that exhibits superelastic properties, wherein the corewire includes a proximal segment and at least one segment that tapers toward a distal end of the corewire; and
    b) an elongated sleeve secured to the corewire such that at least a majority length of the sleeve surrounds at least a portion of the proximal segment of the corewire, the sleeve formed from a second material having a relatively greater stiffness than the first material.
11. The guidewire of claim 10, wherein the first material includes an alloy having nickel and titanium.
12. The guidewire of claim 10, wherein the second material includes stainless steel.
13. The guidewire of claim 11, wherein the second material includes stainless steel.
14. The guidewire of claim 10, wherein the sleeve is generally cylindrical in shape.
15. A method for fabricating a guidewire, comprising the steps of:
    a) providing an elongated corewire formed from a first material;
    b) providing an elongated sleeve formed from a second material having a relatively greater stiffness than the first material;
    c) surrounding at least a portion of the corewire with at least a majority length of the sleeve; and
    d) securing the sleeve to the corewire to fabricate the guidewire.
16. The method of claim 15, wherein the first material exhibits superelastic properties.
17. The method of claim 16, wherein the first material includes an alloy having nickel and titanium.
18. The method of claim 15, wherein the second material includes stainless steel.
19. The method of claim 16, wherein the second material includes stainless steel.
20. The method of claim 15, wherein the sleeve is generally cylindrical in shape.
21. The method of claim 15, wherein the corewire providing step (a) includes the step of providing the corewire with a proximal segment and at least one segment that tapers toward a distal end of the corewire; and
    wherein the surrounding step (c) includes the step of surrounding at least a portion of the proximal segment with at least the majority length of the sleeve.
22. The method of claim 15, including the step of securing a spring to the corewire such that the spring surrounds a distal segment of the corewire.

* * * * *